US010716476B2

(12) United States Patent
Liu et al.

(10) Patent No.: US 10,716,476 B2
(45) Date of Patent: Jul. 21, 2020

(54) METHODS TO IMPROVE AXIAL RESOLUTION IN OPTICAL COHERENCE TOMOGRAPHY

(71) Applicant: NANYANG TECHNOLOGICAL UNIVERSITY, Singapore (SG)

(72) Inventors: Xinyu Liu, Singapore (SG); Linbo Liu, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 420 days.

(21) Appl. No.: 15/509,170

(22) PCT Filed: Oct. 6, 2015

(86) PCT No.: PCT/SG2015/050375
§ 371 (c)(1),
(2) Date: Mar. 6, 2017

(87) PCT Pub. No.: WO2016/056996
PCT Pub. Date: Apr. 14, 2016

(65) Prior Publication Data
US 2017/0290514 A1 Oct. 12, 2017

(30) Foreign Application Priority Data
Oct. 7, 2014 (SG) .............................. 10201406370P

(51) Int. Cl.
*A61B 5/00* (2006.01)
*A61B 3/00* (2006.01)
(Continued)

(52) U.S. Cl.
CPC .......... *A61B 5/0066* (2013.01); *A61B 3/0025* (2013.01); *A61B 3/102* (2013.01);
(Continued)

(58) Field of Classification Search
CPC ..... A61B 5/0066; A61B 3/102; A61B 5/7257; A61B 8/13; G01B 9/02044; G01B 9/02084; G01B 9/02091
See application file for complete search history.

(56) References Cited

U.S. PATENT DOCUMENTS 5,921,929 A * 7/1999 Goll ...................... A61B 8/0875
600/438
5,947,902 A * 9/1999 Goll ...................... A61B 8/0875
600/442

(Continued)

FOREIGN PATENT DOCUMENTS

WO 2012018832 A2 2/2012
WO 2014018950 A1 1/2014
(Continued)

OTHER PUBLICATIONS

E. J. McDowell, M. V. Sarunic, and C. Yang, "1/f Noise in Spectrometer-Based Optical Coherence Tomography," in Biomedical Optics, OSA Technical Digest (CD) (Optical Society of America, 2008), paper BMD79 (Year: 2008).*
(Continued)

*Primary Examiner* — Violeta A Prieto

(57) ABSTRACT

Methods are proposed to improve axial resolution in optical coherence tomography (OCT). In one aspect, the method comprises: obtaining a k-space interferogram of an OCT spectral image; uniformly reshaping the k-space interferogram to a quasi-stationary interferogram by extracting a source envelope; fitting a spectral estimation model to the quasi-stationary interferogram; and calculating an axial depth profile using the fitted spectral estimation model.

4 Claims, 13 Drawing Sheets

(51) Int. Cl.
G01B 9/00 (2006.01)
A61B 8/13 (2006.01)
G01B 9/02 (2006.01)
A61B 3/10 (2006.01)
G01N 21/47 (2006.01)

(52) U.S. Cl.
CPC .................. A61B 5/00 (2013.01); A61B 8/13 (2013.01); G01B 9/02044 (2013.01); G01B 9/02084 (2013.01); G01B 9/02091 (2013.01); G01N 21/47 (2013.01); A61B 5/7257 (2013.01); A61B 2562/0233 (2013.01); A61B 2576/00 (2013.01); G01N 21/4795 (2013.01)

(56) References Cited

U.S. PATENT DOCUMENTS

| | | | | |
|---|---|---|---|---|
| 2006/0244973 | A1* | 11/2006 | Yun | G01B 9/02004 356/511 |
| 2012/0307258 | A1 | 12/2012 | Koerner et al. | |
| 2014/0028997 | A1* | 1/2014 | Cable | G01B 9/02091 356/51 |
| 2017/0074640 | A1* | 3/2017 | Cable | G01B 9/02083 |

FOREIGN PATENT DOCUMENTS

| | | |
|---|---|---|
| WO | 2014040070 A1 | 3/2014 |
| WO | 2016056996 A1 | 4/2016 |

OTHER PUBLICATIONS

Xinyu Liu, Si Chen, Dongyao Cui, Xiaojun Yu, and Linbo Liu, "Spectral estimation optical coherence tomography for axial super-resolution," Opt. Express 23, 26521-26532 (Year: 2015).*

Dongyao Cui, Xinyu Liu, Jing Zhang, Xiaojun Yu, Sun Ding, Yuemei Luo, Jun Gu, Ping Shum, and Linbo Liu, "Dual spectrometer system with spectral compounding for 1-μm optical coherence tomography in vivo," Opt. Lett. 39, 6727-6730 (Year: 2014).*

D. Huang, E. A. Swanson, C. P. Lin, J. S. Schuman, W. G. Stinson, W. Chang, M. R. Hee, T. Flotte, K. Gregory, C. A. Puliafito, and a. et, "Optical coherence tomography," Science 254, 1178-1181 (1991).

M. Wojtkowski, T. Bajraszewski, P. Targowski, and A. Kowalczyk, "Real-time in vivo imaging by high-speed spectral optical coherence tomography," Optics Letters 28, 1745-1747 (2003).

G. Hausler and M. W. Lindner, ""Coherence Radar" and "Spectral Radar"—New Tools for Dermatological Diagnosis," Journal of Biomedical Optics 3, 21-31 (1998).

W. Drexler, U. Morgner, F. X. Kärtner, C. Pitris, S. A. Boppart, X. D. Li, E. P. Ippen, and J. G. Fujimoto, "In vivo ultrahigh-resolution optical coherence tomography," Optics Letters 24, 1221-1223 (1999).

L. Liu, J. A. Gardecki, S. K. Nadkarni, J. D. Toussaint, Y. Yagi, B. E. Bouma, and G. J. Tearney, "Imaging the subcellular structure of human coronary atherosclerosis using micro-optical coherence tomography," Nature Medicine 17, 1010-1014 (2011).

B. Povazay, K Bizheva, A. Unterhuber, B. Hermann, H. Sattmann, A. F. Fercher, W. Drexler, A. Apolonski, W. J. Wadsworth, J. C. Knight, P. S. J. Russell, M. Vetterlein, and E. Scherzer, "Submicrometer axial resolution optical coherence tomography," Opt. Lett. 27, 1800-1802 (2002).

A. N. S. Institute, "American National Standard for Safe Use of Lasers," Z136.1 (2007).

J. M. Schmitt, "Optical coherence tomography (OCT): a review," Selected Topics in Quantum Electronics, IEEE Journal of 5, 1205-1215 (1999).

S. L. Marple Jr, "A tutorial overview of modern spectral estimation," in Acoustics, Speech, and Signal Processing, 1989. ICASSP-89., 1989 International Conference on, (IEEE, 1989), 2152-2157.

R.O. Schmidt, "Multiple emitter location and signal parameter estimation," Antennas and Propagation, IEEE Transactions on 34, 276-280 (1986).

J. Capon, "High-resolution frequency-wavenumber spectrum analysis," Proceedings of the IEEE 57, 1408-1418 (1969).

L. Jian and P. Stoica, "An adaptive filtering approach to spectral estimation and SAR imaging," Signal Processing, IEEE Transactions on 44, 1469-1484 (1996).

T. Yardibi, L. Jian, P. Stoica, X. Ming, and A. B. Baggeroer, "Source Localization and Sensing: A Nonparametric Iterative Adaptive Approach Based on Weighted Least Squares," Aerospace and Electronic Systems, IEEE Transactions on 46, 425-443 (2010).

Y. Takahashi, Y. Watanabe, and M. Sato, "Application of the maximum entropy method to spectral-domain optical coherence tomography for enhancing axial resolution," Appl. Opt. 46, 5228-5236 (2007).

A. Kartakoullis, E. Bousi, and C. Pitris, "Scatterer size-based analysis of optical coherence tomography images using spectral estimation techniques," Optics express 18, 9181-9191 (2010).

S. L. Marple, Jr., "A tutorial overview of modem spectral estimation," in Acoustics, Speech, and Signal Processing, 1989. ICASSP-89., 1989 International Conference on, 1989), 2152-2157 vol.2154.

P. Stoica, E. G. Larsson, and J. Li, "Adaptive filter-bank approach to restoration and spectral analysis of gapped data," The Astronomical Journal 120, 2163 (2000).

Foreign Communication From a Related Counterpart Application, International Search Report and Written Opinion dated Jan. 4, 2016, International Application No. PCT/SG2015/050375 filed on Oct. 6, 2015.

* cited by examiner (a)

(b)

METHODS TO IMPROVE AXIAL RESOLUTION IN OPTICAL COHERENCE TOMOGRAPHY

CROSS-REFERENCE TO RELATED APPLICATIONS

The present application is a filing under 35 U.S.C. 371 as the National Stage of International Application No. PCT/SG2015/050375, filed Oct. 6, 2015, entitled "METHODS TO IM PROVE AXIAL RESOLUTION IN OPTICAL COHERENCE TOMOGRAPHY," which claims priority to Singapore Application No. SG 10201406370P filed with the Intellectual Property Office of Singapore on Oct. 7, 2014 and entitled "METHODS TO IM PROVE AXIAL RESOLUTION IN OPTICAL COHERENCE TOMOGRAPHY," both of which are incorporated herein by reference in their entirety for all purposes.

FIELD OF THE INVENTION

The present invention relates to methods to improve axial resolution in Optical Coherence tomography (OCT).

BACKGROUND

Optical Coherence Tomography

Optical coherence tomography (OCT) [1, 2] is an established in vivo optical imaging technology that provides micrometer resolution and millimeter penetration depth in human tissue. OCT has been widely used clinically to diagnose a wide range of diseases in the retina and the anterior segment of the eye. Recently, intracoronary OCT technology has been used clinically to image coronary artery disease and endoscopic OCT technology has been used for detection of gastrointestinal neoplasm.

Since its invention in 1991, OCT technology has evolved from a time-domain OCT (TD-OCT, first generation technology) [1, 2] to a spectral-domain/Fourier-domain OCT (SD-OCT, second generation technology) [3-7]. The second generation technology provides two to three orders of magnitude higher sensitivity.

However, most of the commercially available OCT technologies are not capable of providing cellular and sub-cellular resolution imaging due to insufficient spatial resolution. For example, the highest resolution commercially available ophthalmic OCT device can provide axial resolution of 8 μm in air [8]. It has been demonstrated in the laboratory that cellular and sub-cellular structures of biological tissues can be reliably visualized using a class of imaging techniques characterized by 1-2 μm axial resolution using repetitive pulsed laser sources and visible light [9-11]. However, these technologies are not clinically and commercially viable because repetitive pulsed laser sources and visible light are subject to more strict safety regulations than the NIR continuous wave (CW) light sources prevalently used in commercial devices [12, 13].

OCT Image Formation

A typical OCT system 20 is illustrated in FIG. 1. In the longitudinal (light propagation) direction, a beamsplitter 22 splits a broadband source field from a light source 24 into a reference field 26 and a sample field 28. The sample field 28 is focused into a small volume in the sample tissue 30. After scattering back from the tissue 30, the sample field 28 modulated with the sample function $E_s$ mixes with the reference function $E_r$ on the surface of a photodetector 32. The sample field 28 and the reference field 26 will interfere in the spectral domain as shown in FIG. 2, and the spectral interference signal $I_D$ is recorded by the detector. The axial (depth) profile 34 of the sample is obtained by use of a Fast Fourier Transform (FFT) on the interference signal $I_D$ as also shown in FIG. 2.

In the spectral (optical frequency) domain OCT, the frequency of interference fringes is dependent on the optical path-length difference between the reference and sample reflectors. For example, the interference signal originated from the sample reflector $r_{S2}$ is carried by a higher frequency than the carrier frequency of the interference signal originated from the sample reflector $r_{S1}$. This means that the sample reflector axial positions are encoded in the spectral interference signal. Therefore, by Fourier transforming the detected spectral interference signal, the axial reflectivity profile of the sample can be obtained.

Axial Resolution of OCT

The axial resolution of an OCT system is defined by the coherence length of the detected light signal which is the full-width-at-half-maximum width of the magnitude of the coherence function defined in Equation (1) below. For example, under Gaussian approximation of spectrum distribution, the measure of the free-space coherence length of the detected light signal is given by [14]:

$$l_c = \frac{2c\ln(2)}{\pi} \cdot \frac{1}{\Delta v} \approx 0.44 \frac{\lambda_0^2}{\Delta\lambda}, \qquad \text{Eq. (1)}$$

where $l_c$ is the full-width of the coherence function at half maximum measured in wavelength units, c is the speed of light, $\Delta v$ is the frequency bandwidth, $\lambda_0$ is the central wavelength of the laser light source and $\Delta\lambda$ is the spectral bandwidth of the light source (at full width half maximum of $E_r$).

From Equation (1) we can determine the following information:
1) Axial resolution can be improved by increasing the spectral bandwidth $\Delta\lambda$ of the detected light signal.
2) Axial resolution of all current OCT technology is limited by the coherence length of the detected light signal.

OCT Light Source

One way to increase the bandwidth of the light source is to combine two light sources with different spectral ranges, for example, a combination of source 1 (700-900 nm) and source 2 (1000-1100 nm). However, this technique is limited by the spectrum discontinuity between source 1 and source 2, because there is a gap in the source spectrum (at 900-1000 nm) which will introduce significant side-lobe artifacts in an axial point-spread function.

Spectral Estimation Techniques

Modern spectral estimation techniques have been developed as alternatives of the Discrete Fourier Transform (DFT)-based method to alleviate its limitations [15]. Generally, these methods can be categorized into two classes: parametric methods, such as autoregressive [15], autoregressive moving average (ARMA) [15], and multiple signal classification (MUSIC) [16] etc., and non-parametric methods, such as Copan [17], amplitude and phase estimation of a sinusoid (APES) [18], and the recently developed iterative adaptive approach (IAA) [19] etc. A previous study that was conducted by Takahashi el., used the maximum entropy method to enhance the depth resolution of OCT [20]. However, the potential of this class of powerful techniques has not been fully explored in OCT imaging [20].

It is therefore an aim of the present invention to provide methods to improve axial resolution in OCT.

SUMMARY OF THE INVENTION

An aim of this invention is to improve axial resolution in OCT. With this common aim in mind, the applicants have developed three methods described in detail herein. Each method in its own right can improve axial resolution in OCT. Furthermore, any combination of the three methods disclosed will further improve axial resolution of OCT.

The first method, referred to herein as the super-resolution method, breaks the coherence-length limit described above by achieving axial resolution higher than the coherence length.

The second method, referred to herein as the spectral combination method, improves axial resolution by extending the spectral bandwidth of OCT by accurately combining multiple spectral bands into one combined spectrum.

The third method, referred to herein as the missing data estimation method, improves axial resolution by filling the gaps between interference signals of discontinuous spectra, thereby reducing side-lobe effects that limit the axial resolution.

Super-Resolution Method

In accordance with a first aspect of the invention there is provided a method to improve axial resolution in OCT comprising:
  a) obtaining a k-space interferogram of an OCT spectral image;
  b) uniformly reshaping the k-space interferogram to a quasi-stationary interferogram by extracting a source envelope;
  c) fitting a spectral estimation model to the quasi-stationary interferogram; and
  d) calculating an axial depth profile using the fitted spectral estimation model.

Thus, embodiments of present invention provide a method for achieving super-resolution in an axial depth profile which is not limited by the coherence-length of the OCT imaging system.

As explained above, conventional OCT imaging has an axial resolution determined by the coherence length of the laser source. Super-resolution spectral estimation techniques cannot be applied to OCT signals because of the non-stationary property of the signals. However, this aspect of the invention uses a uniform reshaping step to make the signals stationary. By using this reshaping step, various modern spectral estimation methods can be used on OCT signals to achieve super-resolution. In summary, this aspect of the invention breaks the coherence-length limitation by adapting OCT signals so that super-resolution algorithms can be utilised, which means that axial resolution higher than the coherence length can be achieved with reduced side-lobe effects.

A spectral estimation technique is once reported to be applied to OCT signals to estimate the scatterer size [21], but has never before been proposed to increase the axial resolution, as per embodiments of the present invention. Furthermore, the maximum entropy method (MEM) has once been applied to enhance the axial resolution by Yoshiyuki [20]. However, the MEM suffers a peak splitting problem when the order is high, which leads to severe artifacts in the image. According to the present aspect of the invention, a uniform reshaping step is used to enable the compatibility of modern spectral estimation techniques and OCT signals. Therefore, the invention breaks the coherence-length limitation by utilising super-resolution modern spectral estimation.

It will be understood that interference signals obtained from an OCT system will be modulated by a spectral envelope of an OCT light source leading to the signals having a non-stationary nature. In order to apply a spectral estimation technique according to embodiments of the invention it is therefore necessary to reshape the interference signals into stationary signals by extracting the source profile.

In embodiments of the invention, the k-space interferogram OCT spectral image may be obtained using existing techniques. For example, a Michelson interferometer-based OCT system may be employed. This is advantageous in that no change to existing hardware is required. Instead, the processing techniques of embodiments of the present invention can be readily applied to the signals obtained from existing equipment.

The spectral estimation model employed may depend on the structure of the sample being tested. In some embodiments, parametric models such as Autoregressive (AR), Autoregression and Moving Average (ARMA), and Subspace estimators may be employed. Typically, AR model spectral analysis methods, including but not limited to nonlinear least squares method, Yule-Walker method, and Burg method [22], works well for layered structures, such as cornea and retina. For high scattering tissue like skin and aorta, ARMA model methods usually give better results than AR methods. Subspace estimators such as MUSIC and the Pisarenko method can also be used for images of high scattering tissue [23]. In other embodiments, non-parametric models such as the Capon method, Amplitude and Phase Estimation of a Sinusoid (APES) and the Iterative Adaptive Approach (IAA) method may provide better results than discrete Fourier transform (DFT) techniques.

The step of uniformly reshaping the k-space interferogram may comprise using a Hilbert transform to extract the envelope A as a function of k and sample depth, d; averaging A(k, d) across the dimension d to obtain the source envelope A(k); and dividing k-space interferogram signal by A(k) to obtain the quasi-stationary interferogram $S_{spre}(k)$. Embodiments of the invention may be useful in imaging cellular structures, for example, in mammalian cornea. Recent evidence shows the corneal endothelium plays an important role in corneal health and most corneal diseases lead to endothelium cell morphology changing, including size, shape and cell density. For example, Fuchs' dystrophy, one of the most common primary endotheliopathies, will enlarge the endothelium cell and decrease the endothelium cell density, accompanying a disfunction of pumping followed by a degradation in barrier function. Secondary corneal endotheliopathes, such as contact lens wear and cornea transplantation, also relate to endothelium changing that can be directly viewed using embodiments of this invention. More specifically, by applying embodiments of this invention, the upper and lower surfaces of the endothelium cells can be resolved along with Descemet's membrane. Accordingly, changing the structure of the endothelium cells can be detected. Embodiments of the present invention can therefore improve the axial resolution of existing ophthalmic OCT systems without any change in hardware. Retinal imaging in vivo using OCT is widely applied clinically and the standard diagnosis procedure has been established over the past two decades.

Spectral Combination Method

In accordance with a second aspect of the invention there is provided a method to improve axial resolution in OCT comprising:
a) obtaining interference signals from two or more different light sources using an OCT device with two or more spectrometers covering two or more source spectral bands with at least one overlapping bandwidth;
b) identifying zero crossing vectors in each signal;
c) aligning the zero crossing vectors of each signal at a first possible position and calculating a sum of the signals in the overlapping bandwidth;
d) repeating step (c) for one, more or each other possible alignment position(s) and identifying the alignment position where the sum of the signals in the overlapping bandwidth is maximal, representing maximal correlation; and
e) combining the interference signals from the different light sources by aligning the zero crossing vectors at the maximal correlation position to extend the spectral bandwidth and thereby improve axial resolution.

It will be understood that a maximal correlation of the signals in the overlapping bandwidth, will correspond to the position where the wavelengths from each source are correctly aligned.

Embodiments of this aspect of the invention therefore improve axial resolution by extending the spectral bandwidth in accordance with Equation (1) above. More specifically, two or more OCT spectral bands can be combined into one complete or gapped spectrum to extend spectral bandwidth using embodiments of the invention. Advantageously, after the spectral combination, the two or more signals will accurately match at each peak or trough in the overlap range.

Accurate coherent combining of two or more spectral bands is impossible in current OCT imaging because the accurate alignment of wavelength is extremely difficult. Embodiments of this aspect of the invention, address this problem by using the zero-crossing vectors of the spectral interference signals obtained from the two or more different light sources as landmarks to accurately align the spectra.

In summary, this aspect of the invention provides a method to combine different spectral bands from different spectrometers thereby achieving ultra-broadband spectrum detection. Embodiments of the invention have been employed to obtain a combined spectrum with a wavelength error less than 0.01 nm. Currently, no existing technology can enable such accurate combination of OCT spectrometers.

In embodiments of the invention, the maximal correlation may be verified by:
i. repeating step a) for a different optical path-length difference between a reference beam and a sample beam to obtain a further set of interference signals;
ii. testing the further set of interference signals by repeating steps (b) to (d), to test if the maximal correlation position obtained previously corresponds to a position identified for maximal correlation of the further set of interference signals.

The different optical path-length can be achieved by axial movement of a sample or reference reflector.

Each zero crossing vector may be assigned an index m (m=1, 2, 3 ... N, with N corresponding to the length of one of the interference signals). The interference signal from source 1 can be denoted as $Z1$ and the interference signal from source 2 can be denoted as $Z2$. In which case, $Z1(1:L+1)$ and $Z2(m:m+L)$ will share the same frequency or wavelength index, where L is the number of zero crossing points inside the overlapping bandwidth. In addition, L may be at least 10 so that the overlapping bandwidth is large enough to allow for accurate alignment. In some embodiments, L may be at least 20, at least 30, at least 40, at least 50 or at least 60.

Linear interpolation may be employed to determine the indices of the zero crossing points.

A spectral background (or DC component) may be subtracted from the interference signals before the zero crossing vectors are identified.

The two or more different light sources may have different center wavelengths or frequencies.

In certain embodiments regression analysis may be employed to determine the position of maximal correlation. The regression analysis may be linear or non-linear.

Missing Data Estimation

In accordance with a third aspect of the invention there is provided a method to improve axial resolution in OCT comprising:
a) obtaining a gapped interference spectrum by combining interference spectra from two or more different sources;
b) estimating an interference pattern for a gap in the spectrum;
c) filling the gap with the estimated interference pattern; and
d) resolving the filled spectrum to retrieve a depth profile with improved axial resolution.

Embodiments of this aspect of the invention aim to eliminate the effect of spectrum gaps between different wavebands when a combined spectrum includes gaps. This is achieved by filling the gaps with estimated data to reduce or eliminate side-lobe artifacts resulting from the gaps in the final OCT image.

Embodiments of the invention can enable the combination of multiple gapped spectral bands to increase the detected spectral bandwidth $\Delta\lambda$, so that the axial resolution can be improved in accordance with Equation (1) above. No existing methods are able to improve axial resolution by use of multiple gapped spectral bands.

The step of estimating the interference pattern for the gap may comprise assuming that the gap and the remainder of the interference spectrum have the same spectral content.

The step of estimating the interference pattern for the gap may comprise using a model such as the gapped-amplitude-and-phase-estimation model (GAPES).

An iterative process may be employed to minimize a least-square criterion between the estimated interference pattern and the remainder of the interference spectrum.

A (weighted) least square method may be employed to fit an initial estimation into an adaptive filter bank model.

A linear prediction model may be used to predict the interference pattern for the gap based on the adaptive filter bank model above.

The adaptive filter bank model may be re-fitted to the filled spectrum using the (weighted) least square method.

The linear prediction model may then be used to get a new prediction for the interference pattern for the gap based on the latest adaptive filter bank model.

The previous two steps may be repeated until a change of the adaptive filter bank model is smaller than a predefined threshold.

The step of resolving the filled spectrum to retrieve the depth profile may comprise use of a Discrete Fourier Transform (DFT) or other spectral analysis technique. For example, the method according to the first aspect of the present invention may be employed.

In accordance with a further aspect of the invention there is provided a non-transitory computer-readable medium having stored thereon program instructions for causing at least one processor to perform the method according to any one or more of the first, second or third aspects of the invention.

BRIEF DESCRIPTION OF THE DRAWINGS

Embodiments of the invention will now be described, by way of example only, with reference to the following drawings, in which.

DETAILED DESCRIPTION

Super-Resolution Method

Figure 1:
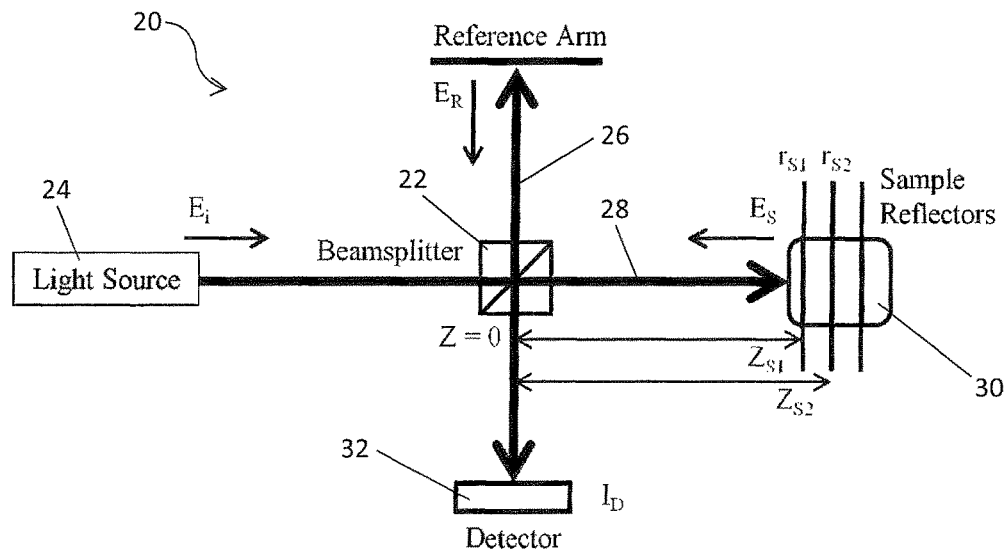
FIG. 1 is a schematic diagram of a known optical coherence tomography system, as discussed in the introduction.
Figure 2:
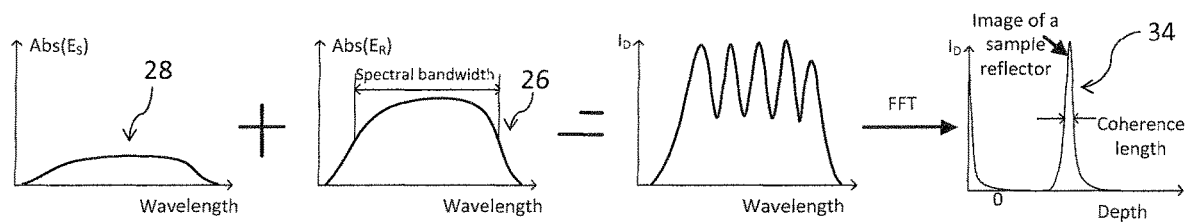
FIG. 2 illustrates the composition of a spectral interferometric signal obtained from the system of FIG. 1 using known techniques to determine an axial depth of a sample reflector, as discussed in the introduction.
Figure 3:
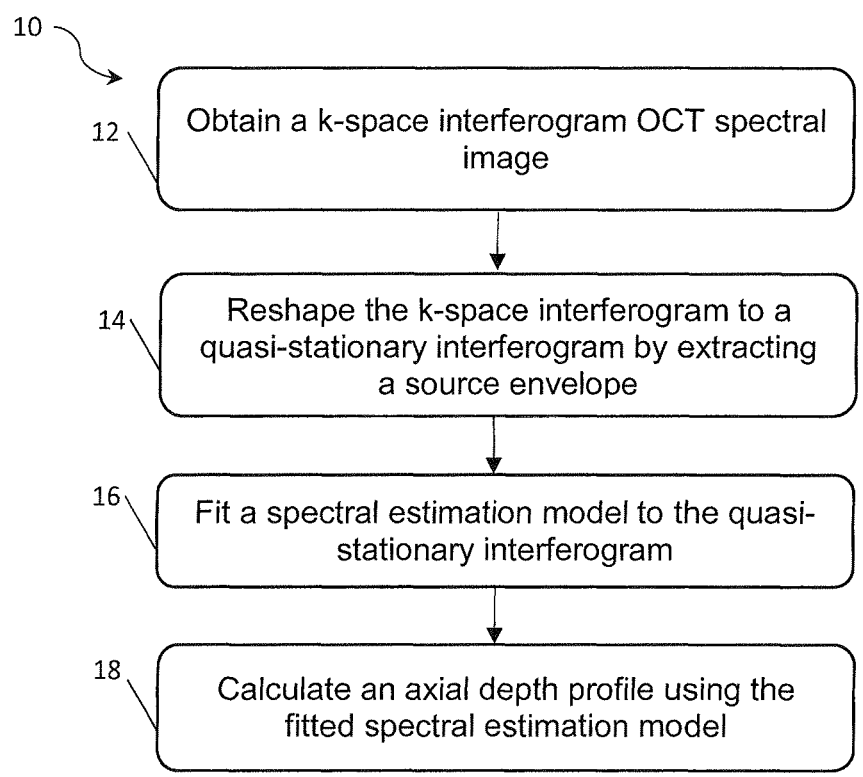
FIG. 3 is a flowchart of a method according to a first aspect of the present invention.

In accordance with a first embodiment of the present invention there is provided a method 10 to improve axial resolution in OCT, as illustrated in FIG. 3. In particular, the method 10 comprises the following steps:

Step 12: obtain a k-space interferogram of an OCT spectral image;

Step 14: uniformly reshape the k-space interferogram to a quasi-stationary interferogram by extracting a source envelope;

Step 16: fit a spectral estimation model to the quasi-stationary interferogram; and Step 18: calculate an axial depth profile using the fitted spectral estimation model.

The method allows the use of modern spectral estimation algorithms in OCT imaging to achieve axial super-resolution, which means axial resolution higher than the coherence length can be achieved.

The interference signals are modulated by the spectral shape of the light source in OCT imaging. This leads to the interference signals being non-stationary which means that modern spectral estimation techniques cannot be applied to OCT signals to enhance the axial resolution. Embodiments of the present invention solve this problem by uniformly reshaping the interference signals to make the signals stationary, thereby enabling the use of various spectral estimation algorithms, thus dramatically improving the axial resolution.

Figure 4:
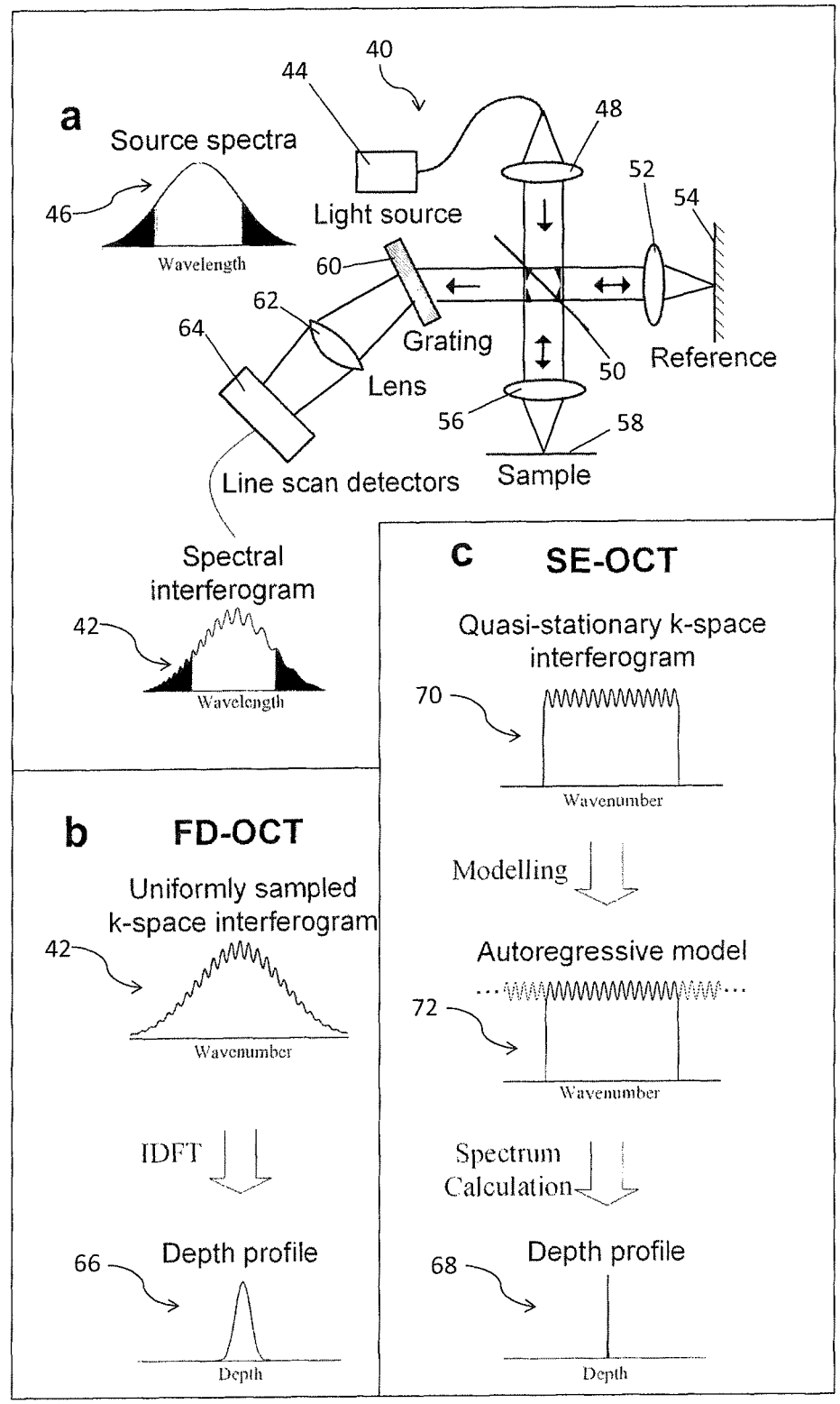
FIGS. 4(a), 4(b) and 4(b) illustrate the principles of (frequency-domain) FD-OCT and (spectral estimation) SE-OCT in accordance with the first aspect of the invention.

FIG. 4(a) shows a Michelson interferometer-based OCT hardware system 40 and the resulting spectral interferogram 42. More specifically, the system 40 comprises a light source 44 having a source spectra 46. Light from the source 44 is passed through a collimating lens 48 to a beamsplitter 50. A reference beam is then directed through a lens 52 to a reference mirror 54 while a sample beam is directed through lens 56 to a sample 58. The reflected beams are then passed through a grating 60 and lens 62 onto a line scan detector 64. FIG. 4(b) shows a traditional Fourier-Domain (FD) OCT analysis method using an inverse Discrete Fourier Transform (DFT) to extract a depth profile 66 from the k-space interferogram 42 of FIG. 4(a). FIG. 4(c) illustrates the spectral estimation (SE) method according to an embodiment of the present invention. In this example, the SE-OCT method uses an autoregressive spectral estimation technique to retrieve the depth profile 68, which includes modeling the reshaped interferogram 70 to an autoregressive model 72 and calculating the depth profile 68 using the model parameters.

As can be seen from FIGS. 4(b) and 4(c), the conventional spectral domain OCT method results in a coherence-limited axial resolution such that the depth profile 66 has a relatively large width. However, in accordance with FIG. 4(c) the spectral analysis method according to embodiments of the present invention results in a significantly improved resolution with a much narrower axial depth profile 68.

In a particular embodiment, the following procedure is followed to achieve super-resolution axial (A-line) profile extraction.

1. Place a single specular reflector at the focal plane of the sample arm 58 of the Michaelson-interferometer (as shown in FIG. 4(a)). Acquire n (n=2, 3, 4, . . . ) spectral interferometric signals $S_{d1}(w)$, $S_{d2}(w)$ . . . $S_{dn}(w)$ at different distances d1, d2, . . . , dn, where w is the source wavelength. These spectral interferometric signals are used to generate a mapping vector V.

2. Extract a phase curve $H_{Sd1}(w)$, $H_{Sd12}(w)$, . . . , $H_{Sdn}(w)$ from the interferometric signal $S_{d1}(w)$, $S_{d2}(w)$ . . . $S_{dn}(w)$ using a Hilbert Transform.

3. Extract a mapping vector V(w) from wavelength space to k-space (wave number or optical frequency space) by eliminating the effect of dispersion and normalisation of $V(w)=(H_{Sd1}(w)-H_{Sd12}(w)$, $H_{Sd3}(w)-H_{Sd14}(w)$, . . . , $H_{Sd(n-1)}(w)-H_{Sdn}(w))/n$;

4. Acquire the spectral interference signal 42 of a sample under investigation. The acquired signal is $S_s(w)$.

5. Remap the interferometric signals $S_s(w)$ from wavelength-linear space to wavenumber-linear space according to the mapping vector V to obtain the k-space signal Ss(k) 42. In this example, the remapping is performed by linear interpolation of $S_s(w)$ on the uniformly sampled wavenumbers k.

6. Remap $S_{d1}(w)$, $S_{d2}(w)$ . . . $S_{dn}(w)$ to wavenumber-linear space to obtain $S_{d1}(k)$, $S_{d2}(k)$ . . . $S_{dn}(k)$ using the same method as per step 5.

7. With $S_{d1}(k)$, $S_{d2}(k)$ . . . $S_{dn}(k)$, use a Hilbert transform to extract the envelope A(k,d) of the k-space signal.

8. Average the A(k,d) in d dimension to obtain the source envelope A(k).

9. To obtain the stationary spectrum signals $S_{spre}(k)$ 72, Ss(k) is divided by A(k); $S_{spre}(k)=Ss(k)/A(k)$;

10. Apply a modern spectral estimation technique to the signal $S_{spre}(k)$ to obtain the super-resolution A-line profile 68 of the sample. Specifically, for example, if an autoregressive model is used, $S_{spre}(k)$ is fitted to an autoregressive process by a modified covariance method [15]. After a model is obtained, the axial depth profile 68 is calculated from the model parameters by the frequency density function [15].

Figure 5:
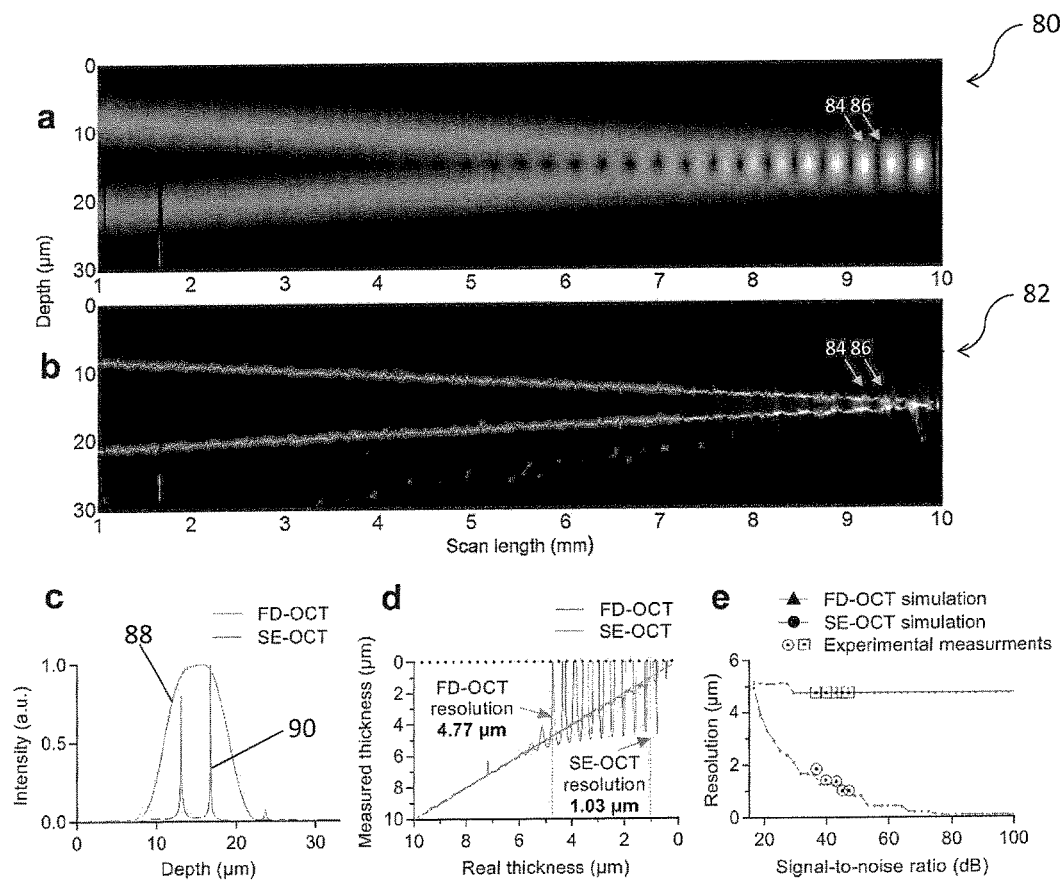
FIGS. 5(a)-(e) show an air wedge between two glass surfaces as imaged with FD-OCT vs. SE-OCT.

FIG. 5 shows a resolution evaluation of embodiments of the invention. The cross-sectional images 80, 82 of an air wedge between two glass surfaces are illustrated using traditional FD-OCT in FIG. 5(a) and SE-OCT according to an embodiment of the present invention in FIG. 5(b). Thus, it can be seen that much higher resolution is achieved in FIG. 5(b) and the side-lobe effects broadening the lines in FIG. 5(a) are eliminated in FIG. 5(b). See, for comparison, points indicated by arrows 84 and 86 in FIGS. 5(a) and 5(b).

FIG. 5(c) shows normalized depth line profiles for both images at a scan length of 7.5 mm. This shows that a single broad FD-OCT line profile 88 can be resolved to show two much narrower line profiles 90 using SE-OCT. FIG. 5(d) shows measured wedge thickness using FD-OCT and SE-OCT as a function of the calculated true thickness. This again, shows the much higher resolution achievable with SE-OCT. FIG. 5(e) shows plots of depth resolution for both methods as a function of the signal-to-noise ratio predicted by numerical simulation, with verifying experimental results (where squares represent FD-OCT; circles represent SE-OCT). In embodiments of the invention, different modern spectral estimation methods may be employed including parametric methods (e.g. Autoregressive (AR), Autoregression and Moving Average (ARMA), and Subspace estimators), and non-parametric methods, chosen according to the structure of the sample. Typically, AR model spectral analysis methods, including but not limited to nonlinear least squares method, Yule-Walker method, and Burg method [22], work well for layered structures, such as cornea and retina. For high scattering tissue like skin and aorta, ARMA model methods usually give better result than AR methods. Subspace estimators such as MUSIC and the Pisarenko method can also be used for images of high scattering tissue [23]. Non-parametric methods such as the Capon method, Amplitude and Phase Estimation of a Sinusoid (APES) and Iterative Adaptive Approach (IAA) method, can also provide better results than DFT for various sample structures.

Figure 6:
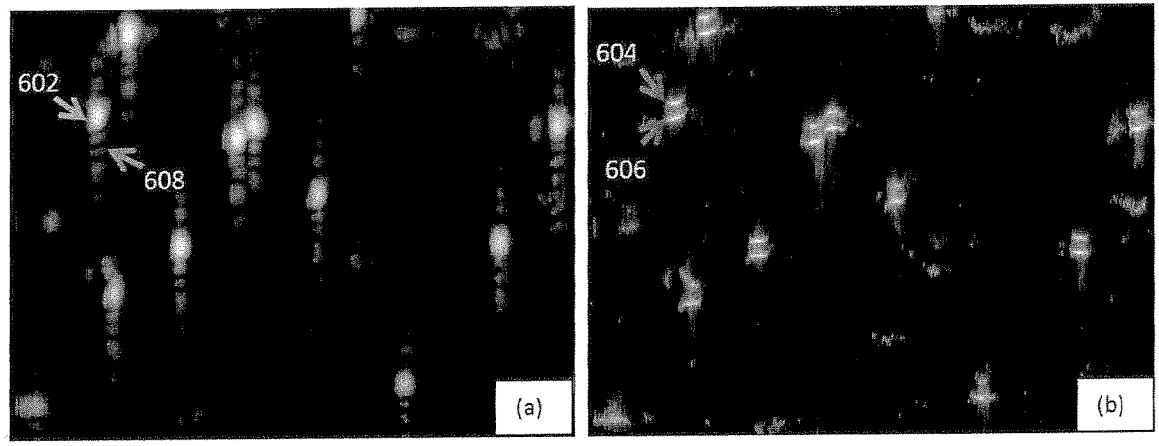
FIG. 6(a) shows An image of 2 micron particles obtained using a known DFT method.
FIG. 6(b) an image obtained using the proposed spectral estimation method.

FIG. 6 shows images of polystyrene beads (2 micrometers in diameter) in water using an existing SD-OCT device (for example as shown in FIG. 4(a)). The results obtained using traditional DFT are shown in FIG. 6(a) alongside the results of the proposed spectral analysis method in FIG. 6(b). Since the coherence-length limited axial resolution of the SD-OCT device was measured at 4.05 micrometer in air, the DFT method is not able to resolve the top and bottom surface of individual beads as shown in FIG. 6(a) by arrow 602. In contrast, using the same spectral interference signal, the proposed spectral analysis method can clearly resolve the top (arrow 604) and bottom (arrow 606) surface of the individual bead as shown in FIG. 6(b). Accordingly, the present method is able to break the coherence-length limitation of any OCT setup in existence. In addition, the side-lobe artifacts (arrow 608 in FIG. 6(a)) are completely suppressed in FIG. 6(b).

In accordance with embodiments of the invention, it is possible to improve the axial resolution of an existing SD-OCT system so that cellular structures, for example, in mammalian cornea can be visualized. Recent evidence shows the corneal endothelium plays an important role in corneal health and most corneal diseases lead to endothelium cell morphology changing (including size, shape and cell density). For example, Fuchs' dystrophy, one of the most common primary endotheliopathies, will enlarge the endothelium cell and decrease the endothelium cell density, accompanying a disfunction of pumping followed by a degradation in barrier function. Secondary corneal endotheliopathies, such as contact lens wear and cornea transplantation, also relate to endothelium changing that can be directly viewed by embodiments of this invention.

Figure 7:
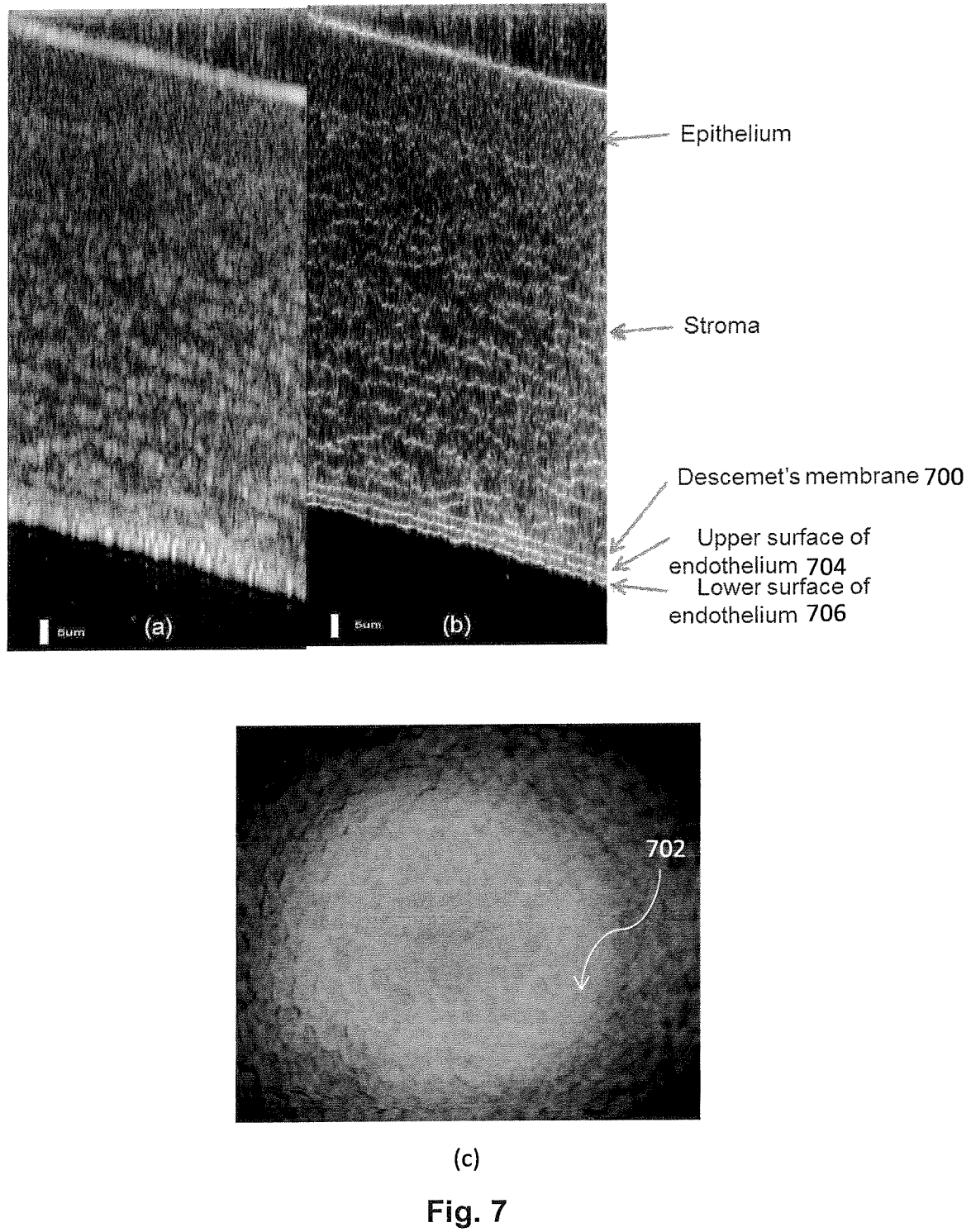
FIG. 7(a) shows an ex vivo image of the rat cornea using an existing SD-OCT device.
FIG. 7(b) shows applying the super-resolution method according to the first aspect of the invention.
FIG. 7(c) shows showing an en face image of the endothelium cell.

FIG. 7(a) shows an ex vivo rat cornea imaged using an existing SD-OCT system and DFT analysis. Descemet's membrane 700 and the endothelium layer at the bottom of cornea cannot be clearly differentiated. However, after applying an embodiment of the proposed super-resolution algorithm, the above mentioned two layers can be clearly visualized as shown in FIG. 7(b). The en face image shows that the endothelium cells 702 can be clearly recognised by the proposed method (FIG. 7 (c)). By applying the proposed method, the upper and lower surfaces 704, 706 of the endothelium cells 702 can be resolved, enabling the en face viewing of the lower surface of the endothelium cells, at which layer the hexagonal cell shape can be clearly seen. Thus, embodiments of the present invention can improve the axial resolution of existing ophthalmic OCT systems without any change in hardware. Retinal imaging in vivo using OCT is widely applied clinically and the standard diagnosis procedure has been established over the past two decades. Embodiments of the present invention can be applied to any captured OCT images to improve the image resolution and permit better diagnosis.

Figure 8:
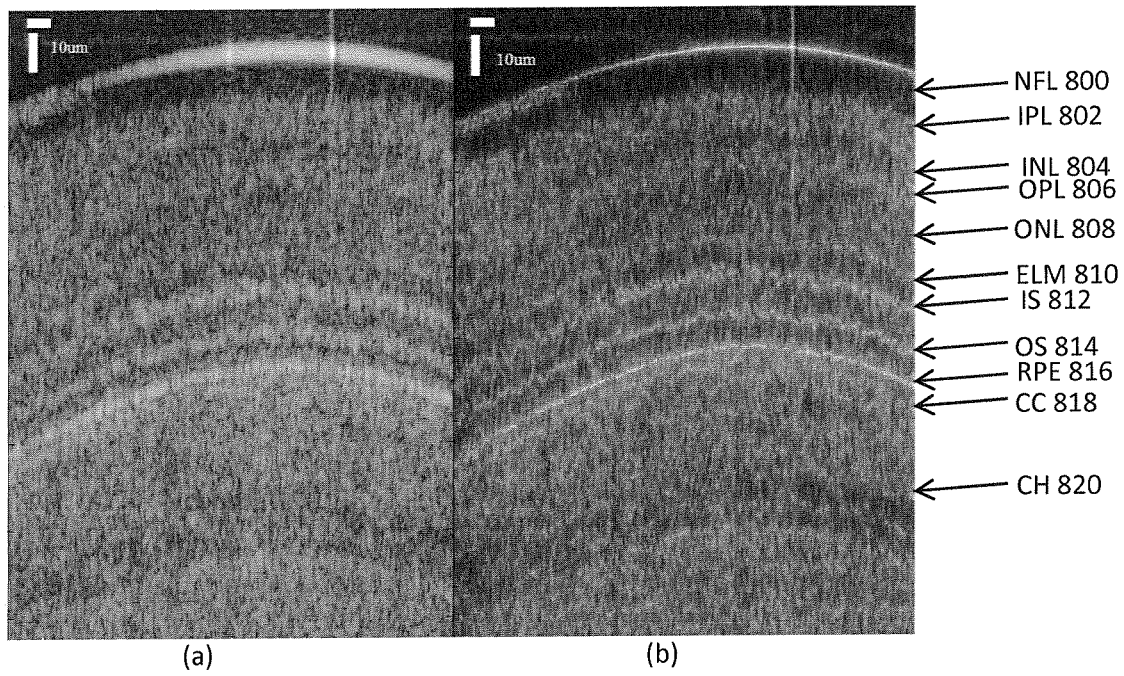
FIG. 8(a) shows a comparison between retina images obtained using the existing processing method and FIG. 8(b) the super-resolution method according to the first aspect of the invention.

FIG. 8(a) shows a rabbit retinal image obtained using the existing processing method (DFT). For comparison, FIG. 8(b) shows the same image obtained by applying the super-resolution algorithm according to embodiments of the invention. With the increase in resolution provided in FIG. 8(b), the following layers can be clearly distinguished: nerve fiber layer (NFL) 800; inner plexiform layer (IPL) 802; inner nuclear layer (INL) 804; outer plexiform layer (OPL) 806;

outer nuclear layer (ONL) 808; external limiting membrane (ELM) 810; inner segment (IS) 812; outer segment (OS) 814; retinal pigment epithelium (RPE) 816; choirocapillaris (CC) 818; and choroid (CH) 820.

Figure 9:
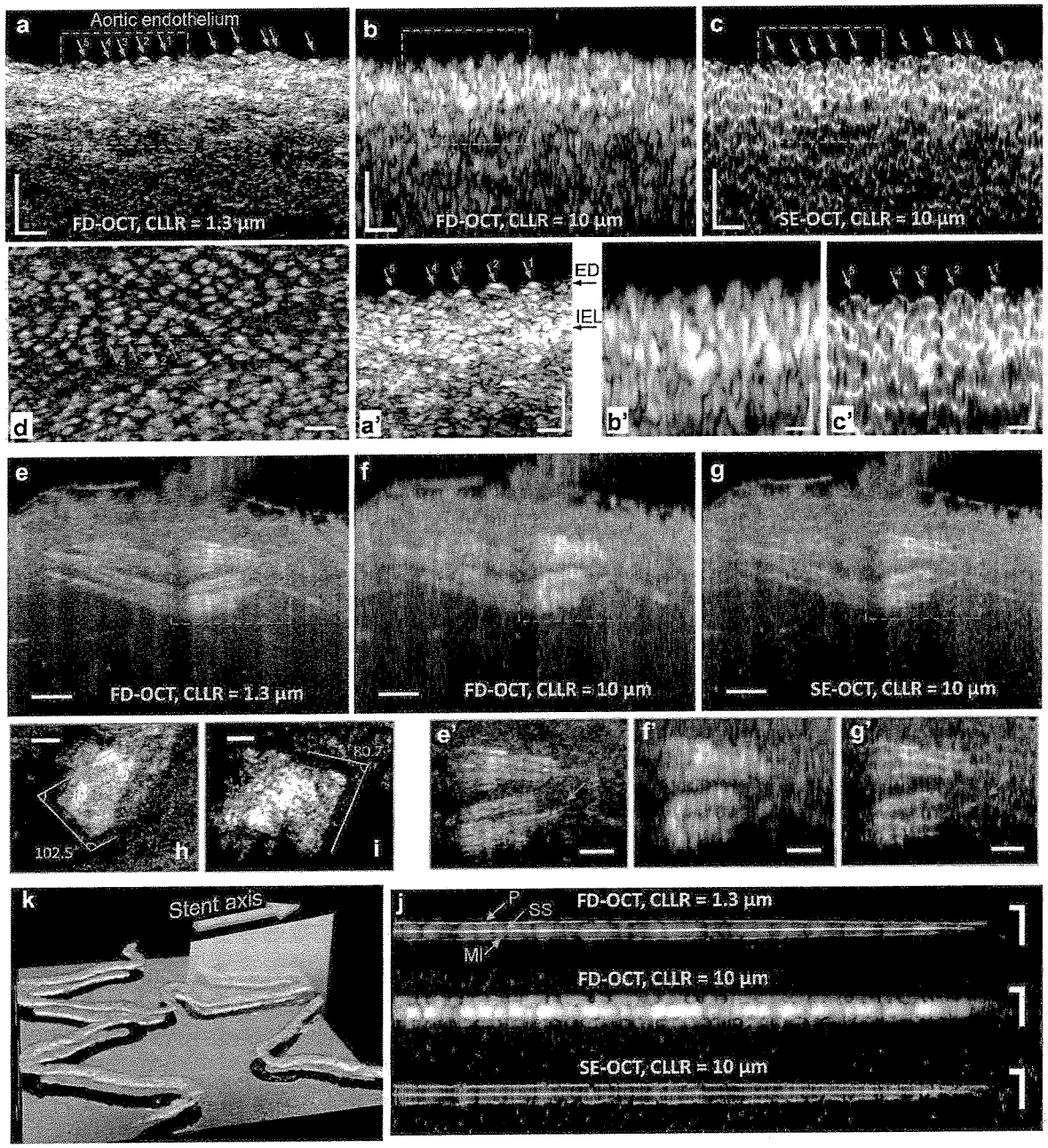
FIGS. 9(a)-(q) show a variety of OCT images that have been processed using either the known DFT method or the super-resolution method according to the first aspect of the invention so that the axial resolution in each image can be compared.

FIG. 9 shows comparisons for swine aortic tissue, human atherosclerotic aortic tissue and drug-eluting stents using traditional FD-OCT and SE-OCT according to embodiments of the present invention. In particular, FIGS. 9(a), (b) and (c) show respectively cross-sectional images of a fresh swine aortic tissue imaged using 1.3-μm coherence-length limited resolution (CLLR) FD-OCT, 10-μm coherence-length limited resolution FD-OCT, and 10-μm coherence-length limited resolution SE-OCT. Furthermore, FIGS. 9(l)-9(n) show magnified views of the aortic endothelium within the dashed boxes in FIGS. 9(a), (b) and (c). In FIG. 9(l) the endothelium (ED) and internal elastic lamina (IEL) layers are indicated. In addition, FIG. 9(d) shows the en face plane of the surface of the swine aorta using flattened 1.3-μm FD-OCT images. From these images a pavement-like arrangement and consistent cell orientation can be seen confirming that the bright 'caps' in FIGS. 9(l) and 9(n) were endothelial cells. The dotted line in FIG. 9(d) indicates the location where the cross-sectional images (a), (b) and (c) were taken. From these images it is clear that the 10-μm coherence-length limited resolution SE-OCT are much clearer than the 10-μm coherence-length limited resolution FD-OCT and much closer to the level of detail visible in the 1.3-μm coherence-length limited resolution FD-OCT images. Thus confirming that SE-OCT has a resolution that is better than that which is achievable in a comparable FD-OCT method which is limited by the coherence-length.

FIGS. 9(e), (f) and (g) show cross-sectional images of a human atherosclerotic plaque produced respectively by the 1.3-μm coherence-length limited resolution FD-OCT, the 10-μm coherence-length limited resolution FD-OCT, and the 10-μm coherence-length limited resolution SE-OCT. As above, FIGS. 9(o)-9(q) show magnified views of cholesterol crystals within the dashed boxes in FIGS. 9(e), (f) and (g) respectively. Furthermore, FIGS. 9(h) and (i) show measured angles confirming two cholesterol crystal plates indicated by the arrows in FIGS. 9(o) and 9(q) respectively. Thus, again, the SE-OCT images have a better resolution than those that are coherence-length limited through use of an equivalent FD-OCT method. FIG. 9(k) shows a three-dimension rendered view of drug-eluting stent struts taken from a 1.3-μm coherence-length limited resolution FD-OCT image. The plane indicates the position of the cross-sectional images in FIG. 9(j) for each of the three processes: 1.3-μm coherence-length limited resolution FD-OCT; 10-μm coherence-length limited resolution FD-OCT; and 10-μm coherence-length limited resolution SE-OCT. In FIG. 9(j) the polymer (P), stent strut (SS) and mirror image (MI) are indicated. This image once more shows the greater resolution achievable using the SE-OCT method according to embodiments of the present invention, when compared to an equivalent CLLR FD-OCT system.

For reference, the scale bars in FIG. 9 are as follows: (a-d) 40 μm, (I-n, h & i) 20 μm, (e-g) 50 μm, (o-q) 30 μm.

Spectral Combination Method

In accordance with the second aspect of the invention, there is provided a method to improve axial resolution by accurately and coherently combining two or more spectral bands. This method enables ultra-broadband detection for OCT technology in favor of axial resolution.

Figure 10:
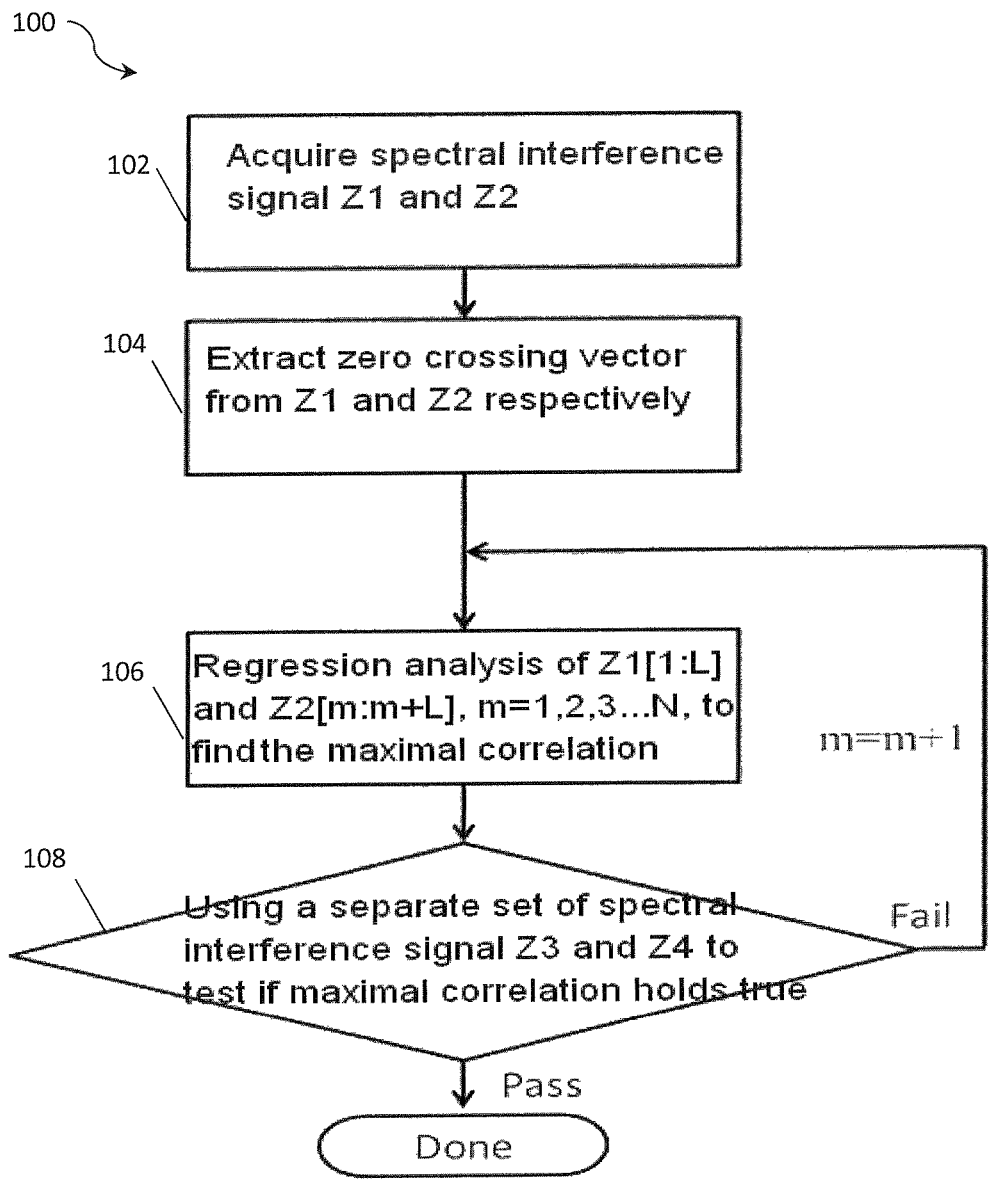
FIG. 10 shows a flowchart of a method according to a second aspect of the present invention.

As illustrated in FIG. 10, the method 100 comprises:
Step 102: obtaining interference signals (Z1 and Z2) from two or more different light sources using an OCT device;
Step 104: extracting zero crossing vectors from each signal (Z1 and Z2);
Step 106: applying regression analysis to the extracted signals Z1[1:L+1] and Z2[m:m+L], where m=1, 2, 3, . . . N and N is the length of the interference signal Z2, to find maximal correlation and combining the interference signals from the different light sources by aligning the zero crossing vectors at the maximal correlation to extend the spectral bandwidth and thereby improve axial resolution, where L is the number of zero crossing points inside the overlapping region.

As illustrated in FIG. 10, there may be a further verification step 108 of using a separate set of spectral interference signals Z3 and Z4 to test whether the maximal correlation holds true. If it does not, step 106 is repeated with m=m+1. If it does hold true the maximum correlation has been found and can be used for mapping the two spectral bands into one broadband before determining the axial resolution.

It should be understood that accurate coherent combining of two spectral bands is difficult because there are no wavelength landmarks that can be used for the mapping of the two spectral bands. Using a narrowband calibration laser can provide only one landmark and the bandwidth of the calibration laser limits the accuracy of combination.

This problem is solved by the present method. In embodiments of the invention, spectral interference signals are obtained using two mirrors. The zero-crossings of the background subtracted spectral interference signal can be used as accurate landmarks to align the two spectra. Axial scanning of one mirror provides numerous landmarks that can be used to accurately align the two spectra with a wavelength error of less than 0.01 nm.

As shown in FIG. 10, to combine two interference spectra, firstly, the interference signals Z1 and Z2 are obtained using the same OCT device from two light sources of different center wavelength or frequency. Secondly, after background subtraction (e.g. removing a DC component), the zero crossing vectors are extracted from both Z1 and Z2. Thirdly, regression analysis, linear or non-linear, is applied to the subset of Z1 and Z2:Z1 (1:L+1) and Z2(m:m+L) to find the maximal correlation where L is the number of zero crossing points inside the overlapping region. In the fourth step, the step one is repeated for a different optical path-length difference between the reference and the sample arm to obtain a separate set of interference signal Z3 and Z4. Z3 and Z4 are then used to test if maximal correlation holds true between Z3 (1:L+1) and Z4(m:m+L). If not, the program goes back to the third step to find the next maximal correlation. If yes, the spectral combination is done.

Figure 11:
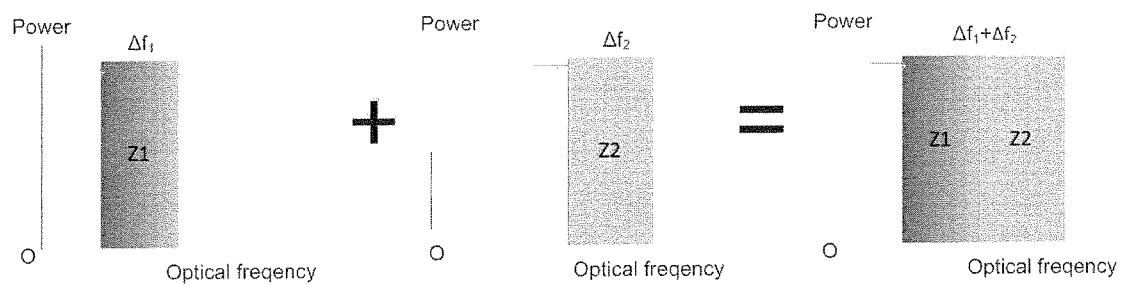
FIG. 11 shows the principle of combining two optical spectra in accordance with the second aspect of the invention.
Figure 12:
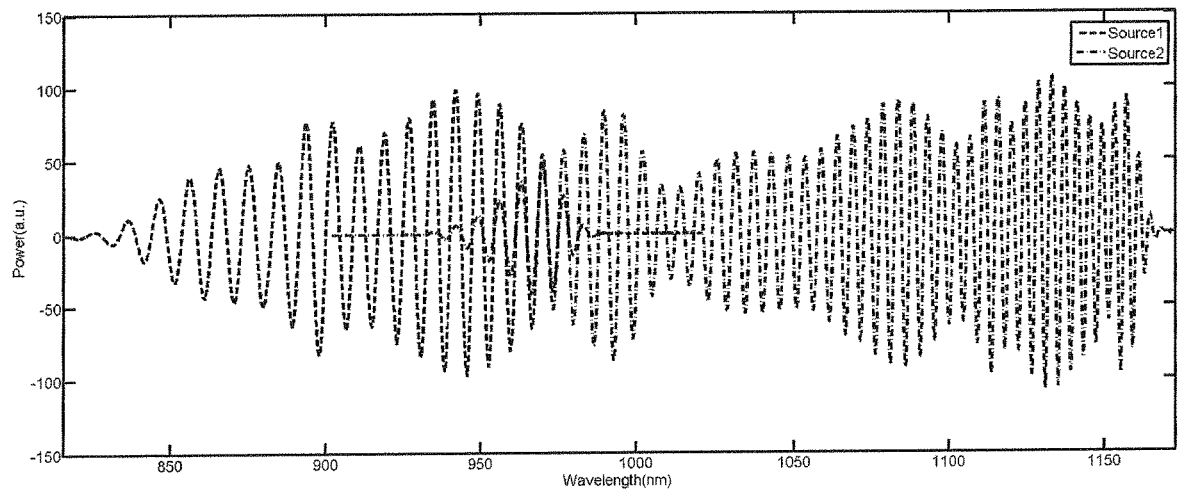
FIG. 12 illustrates how two spectra are combined in accordance with the second aspect of the invention.

The concept of spectral combination is illustrated in FIG. 11. Two spectral interference signals Z1 and Z2 are combined into one interference signal in order to extend the spectral bandwidth. In most OCT setups, since the spectrometer is not calibrated, the absolute frequency or wavelength indices of the interference spectra Z1 and Z2 are not known. If Z1 and Z2 overlap in a spectral region, an index m (m=1, 2, 3 . . . N, N being the length of the interference signal Z2) can be found so that Z1 (1:L+1) and Z2(m:m+L) share the same frequency or wavelength index. For example, in FIG. 12 Z1 (-- signal) is acquired from an OCT device using light source 1 and Z2 (-.- signal) is acquired from the same OCT device using source 2. After spectral combination, the two signals match perfectly at each peak or valley inside the overlap range. This is achieved through the method described in FIG. 10.

Missing Data Estimation

Figure 13:
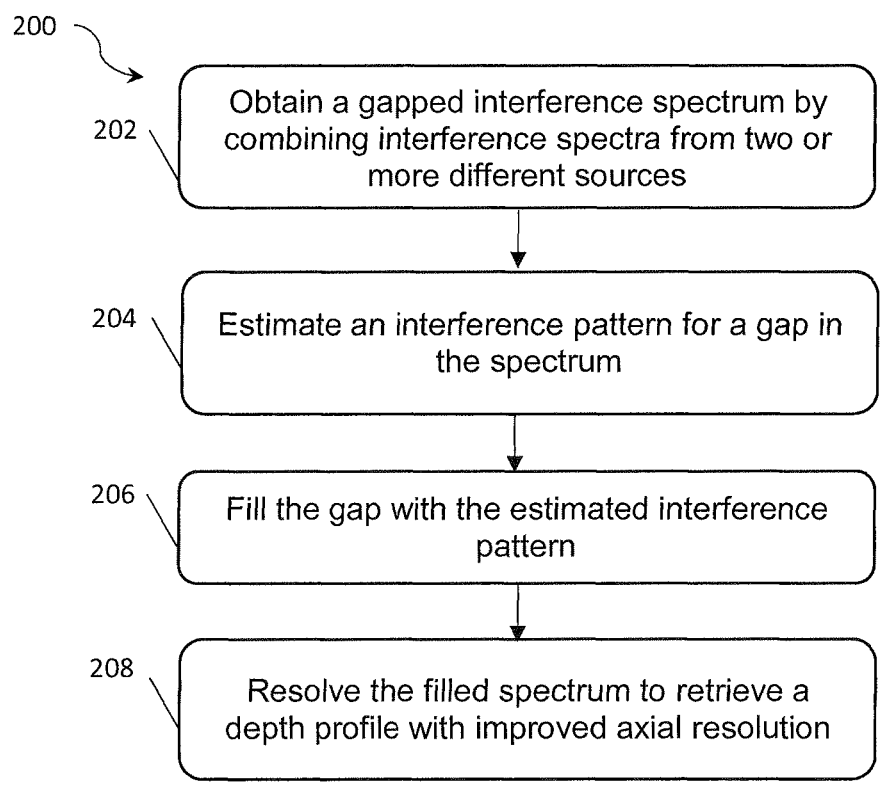
FIG. 13 shows a flowchart of a method according to a third aspect of the present invention.

In accordance with the third aspect of the invention, there is provided a further method to improve axial resolution in OCT. The method 200 is illustrated in FIG. 13 and comprises the following steps:

Step 202: obtain a gapped interference spectrum by combining interference spectra from two or more different sources;
Step 204: estimate an interference pattern for a gap in the spectrum;
Step 206: fill the gap with the estimated interference pattern; and
Step 208: resolve the filled spectrum to retrieve a depth profile with improved axial resolution.

In particular embodiments of the invention, a known algorithm called gapped amplitude and phase estimation (Gapped-APES) [24] is employed to estimate the missing part of the gapped spectrum. This results in a continuous spectrum which produces much less side-lobe artifacts and higher axial resolution. Embodiments of this method promise to bridge various bands used by different OCT systems to thereby obtain a virtual broadband spectrum in favour of a high axial resolution.

Figure 14:
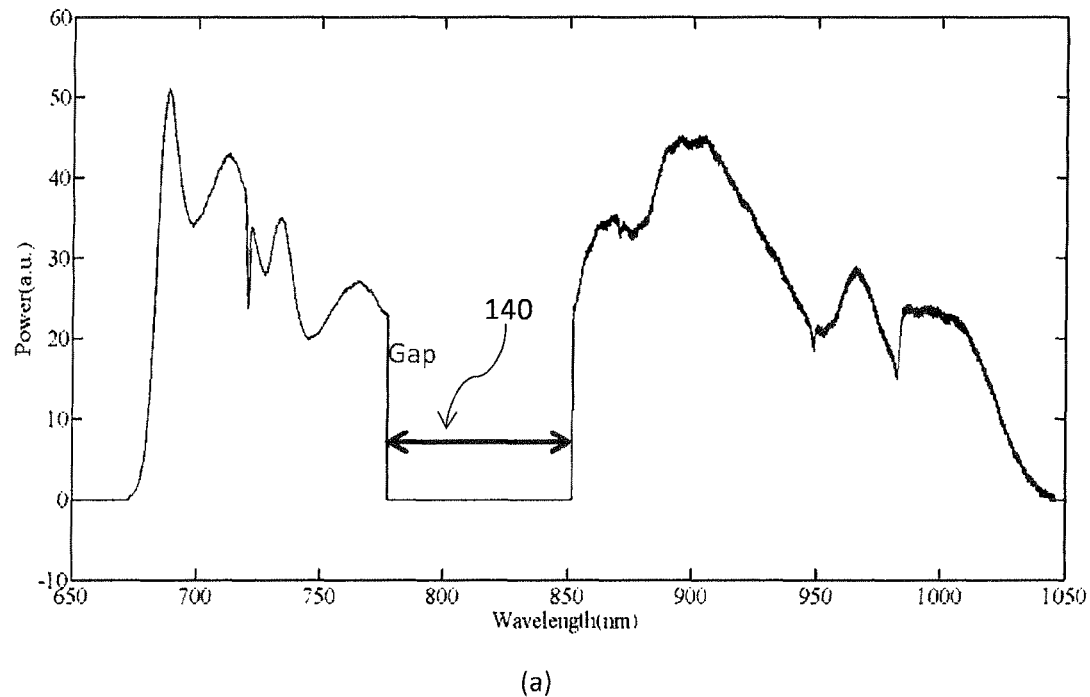
FIG. 14(a) shows a gapped spectrum of an OCT device and FIG. 14(b) a depth profile of a stack of glass slides obtained from the gapped spectrum (dotted line) and the missing data estimation method according to the third aspect of the present invention (solid line)
Figure 14:
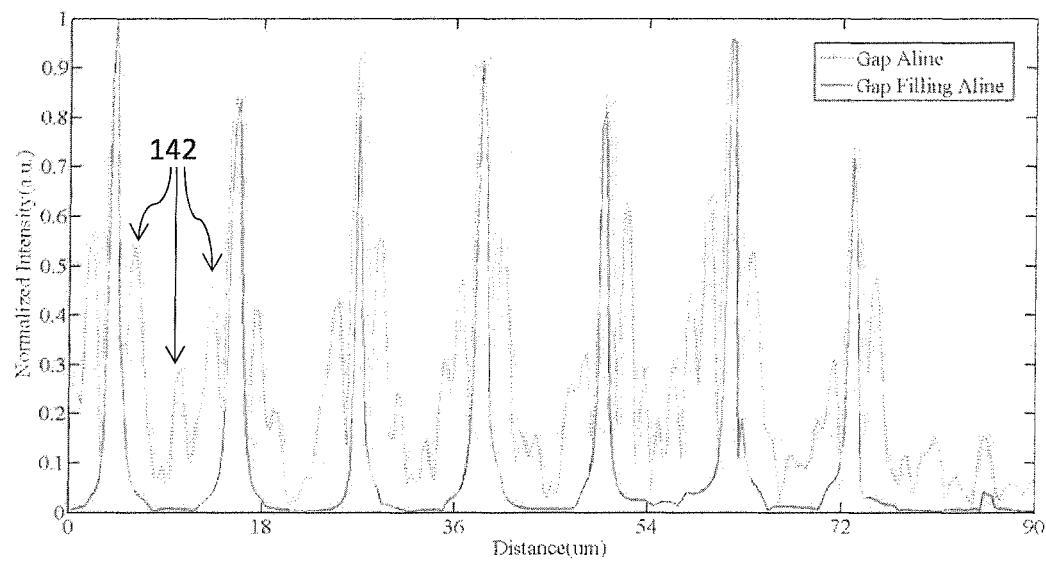

FIG. 14 shows an example of the proposed missing data estimation method. The sample comprises a stack of glass slides of nearly 10 um thickness. The spectrum of the input light source has a gap 140 in the middle as shown in FIG. 14(a) which leads to huge side-lobes 142 in the point spread function of the image as shown in FIG. 14(b) by the dotted line. By use of a missing data estimation technique according to this aspect of the invention, the side-lobe artifacts 142 can be eliminated without any degradation on the resolution as shown in FIG. 14(b) by the solid line.

A more detailed description of an embodiment of this method is as follows:

1. Process a sample spectral signal to obtain an initial estimation $S_{spgap}(k)$ for the gap.
2. Using a weighted least square method, fit $S_{spgap}(k)$ into an adaptive filter bank model.
3. Using a linear prediction method predict the values in the gap, based on the adaptive filter bank model obtained in step 2. In this way, the gaps are filled with data containing the same spectral content as the non-gapped data (from which the sample was taken). The whole spectrum signal is $S_{sp}(k)$ without gaps.
4. Refit the adaptive filter bank model to the $S_{sp}(k)$ spectrum using a weighted least square method. Repeat step 3 to get a new set of $S_{sp}(k)$ data with a new prediction of the gaps.
5. Repeat step 4 until the change of the adaptive filter bank model is smaller than a preset value during two adjacent iterations to obtain the final spectral data $Sg_f(k)$.
6. Apply DFT or other appropriate spectral analysis technique to $Sg_f(k)$ to obtain the super-resolution axial line profile of the sample.

To demonstrate this method, the applicants used a free-space Michelson interferometer based OCT system, as illustrated in FIG. 4(a), illuminated by a super-luminescent diode array SLD with three separately controllable diodes. The second diode was turned off to obtain a gapped light spectrum. This resulted in degradation in axial resolution and a huge increase of side-lobe artifacts compared to when the full spectrum was used. Using the gapped-APES method described above, the missing band was restored under the assumption that the missing part and available parts have the same spectral contents. By iteratively conducting amplitude and phase estimation and minimizing a least-square criterion between the spectrum of estimated data and the spectrum of original available data, an estimation of the data in the gap band was determined. The spectrum including the estimated (missing) data was then used to retrieve a depth profile, showing better performance than using the gapped spectrum.

Figure 15:
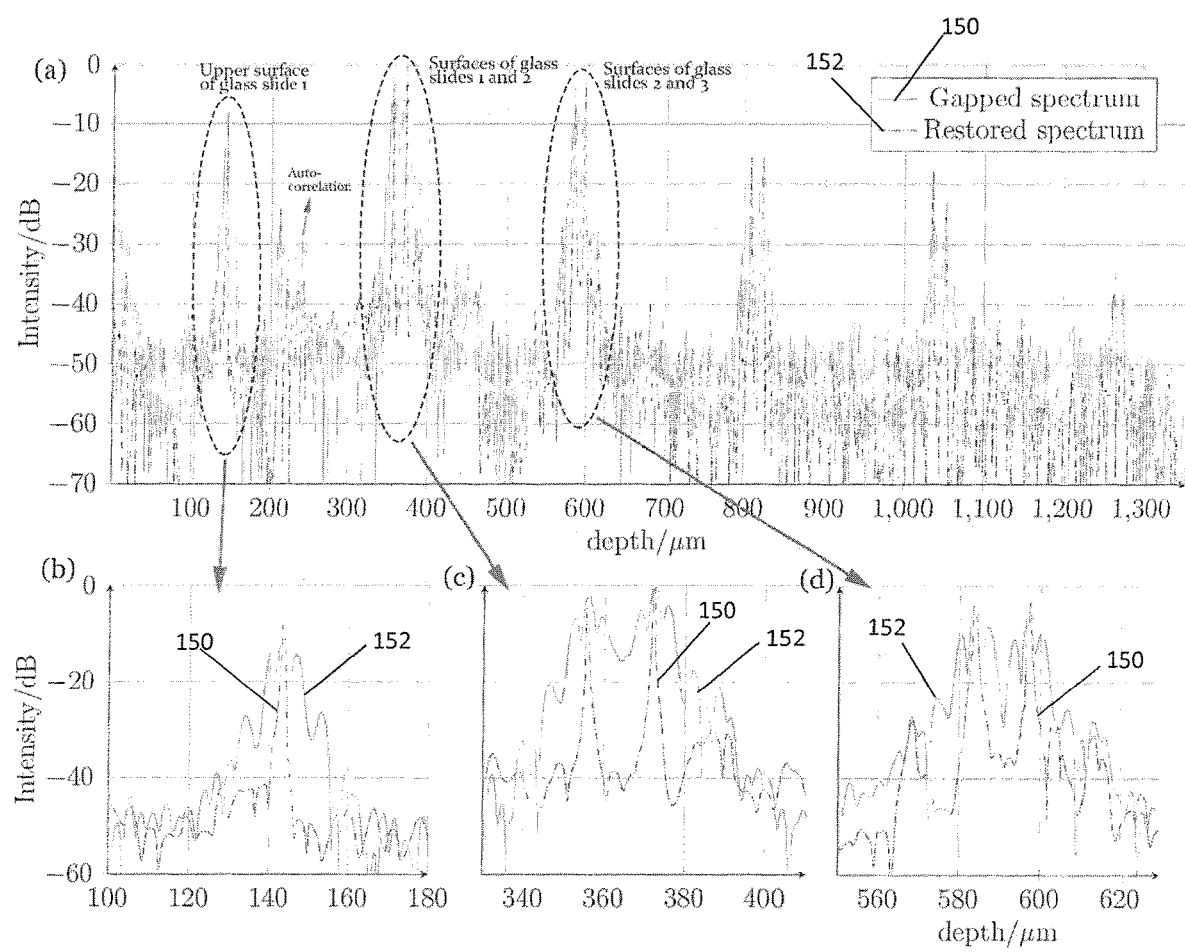
FIG. 15(a) shows a glass stack image of a full depth profile (as obtained from a gapped spectrum and a filled spectrum) and enlarged images for individual glass plates FIGS. 15(b), 15(c) and 15(d)

FIG. 15(a) shows an image of a stack of multiple glass slides (of thickness 0.2 mm) as used to evaluate the A-line profile. A comparison is made of the A-line profile in logarithm scale of both the restored spectrum 150 and the gapped spectrum 152. FIGS. 15(b), (c) and (d) show enlarged images of three of the glass slide interfaces showing an improvement of resolution and suppression of side-lobes using the restored spectrum 150 as opposed to the original gapped spectrum 152.

Figure 16A:
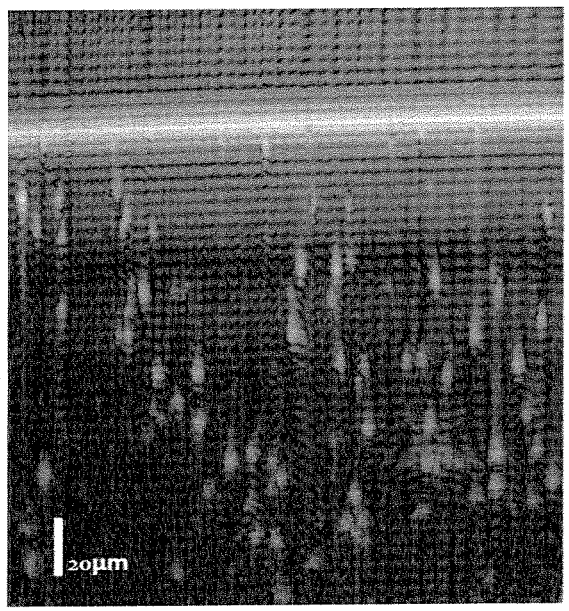
FIG. 16(a) shows OCT images of polystyrene particles in water where image is retrieved from gapped spectrum and image
Figure 16B:
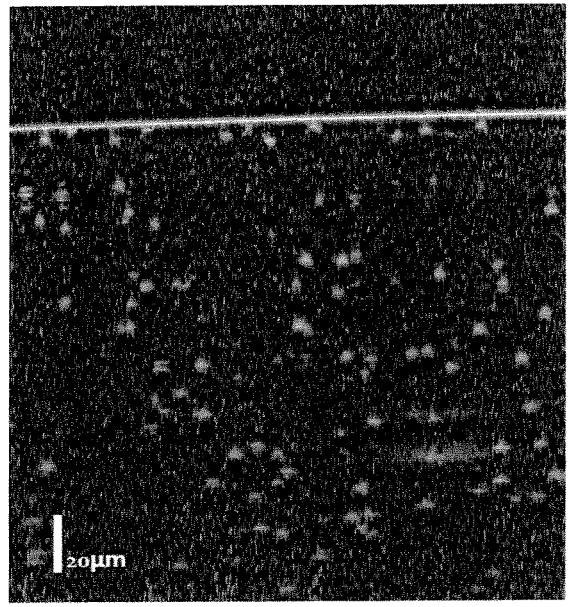
FIG. 16(b) is retrieved from a restored spectrum in accordance with the third aspect of the invention.

FIGS. 16(a) and 16(b) show images of polystyrene calibration particles (of diameter 2 μm) in water. This time the sample was imaged with a full spectrum and a middle ⅓ section of the acquired data was set to zero to simulate a gapped spectrum. In this case, it can be seen that the severe side-lobe artifacts in the gapped data image of FIG. 16(a) are completely suppressed in the restored data image of FIG. 16(b).

Figure 17A:
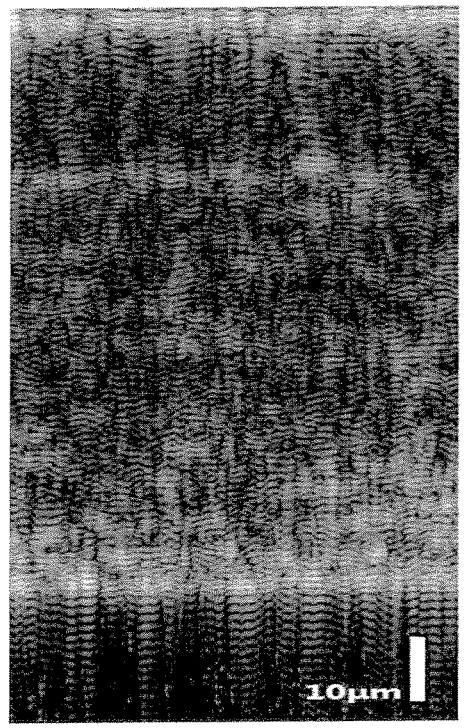
FIG. 17(a) shows OCT images of rat eye cornea ex vivo where image is retrieved from gapped spectrum and image
Figure 17B:
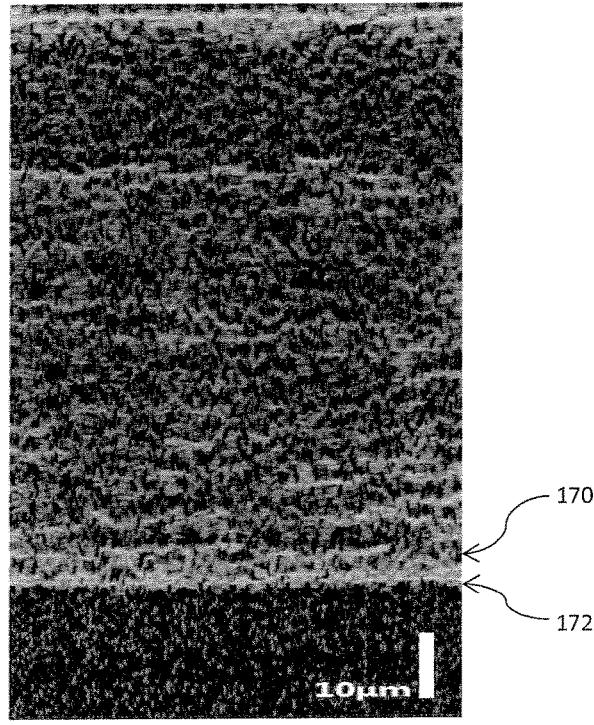
FIG. 17(b) is retrieved from a restored spectrum in accordance with the third aspect of the invention.

As another example, a rat eye cornea was imaged ex vivo in full spectrum and the middle ⅓ section of the detected signal was set to zero to simulate a gapped spectrum. In this case, it can be seen that the gapped image of FIG. 17(a) is so blurred that the layer structures cannot be identified. However, in the restored spectrum image of FIG. 17(b), the side-lobe artifacts are very well suppressed and it is possible to identify Descemet's membrane 170 and endothelium cells 172 at the bottom of the cornea. This improvement therefore makes measurement of the layer thickness and morphology analysis possible in clinical use.

Commercial Applications

Embodiments of the invention can be commercialised for clinical diagnosis of various eye diseases. Clinical applications of this invention can also expand to intracoronary imaging and endoscopic imaging for diagnosis of coronary artery disease and gastrointestinal cancers respectively. Since the application of a spectral analysis algorithm does not require any change in the hardware, in principle axial resolution of all the existing SD-OCT and swept-source OCT devices can be improved by embodiments of the invention.

Although only certain embodiments of the present invention have been described in detail, many variations are possible in accordance with the appended claims.

REFERENCES

The disclosures of the following references are incorporated herein in their entirety.

1. D. Huang, E. A. Swanson, C. P. Lin, J. S. Schuman, W. G. Stinson, W. Chang, M. R. Hee, T. Flotte, K. Gregory, C. A. Puliafito, and a. et, "Optical coherence tomography," Science 254, 1178-1181 (1991).
2. E. A. Swanson, "U.S. Pat. No. 5,321,501" (1994).
3. M. Wojtkowski, T. Bajraszewski, P. Targowski, and A. Kowalczyk, "Real-time in vivo imaging by high-speed spectral optical coherence tomography," Optics Letters 28, 1745-1747 (2003).
4. G. Hausler and M. W. Lindner, ""Coherence Radar" and "Spectral Radar"—New Tools for Dermatological Diagnosis," Journal of Biomedical Optics 3, 21-31 (1998).
5. J. M. Schmitt, "U.S. Pat. No. 7,916,387," (2008).
6. S. H. Yun, "US20090027689," (2011).

7. J. F. deBoer, "U.S. Pat. No. 7,872,757," (2011).
8. T. Corporation, "DRI OCT-1 technical specifications:," http://www.topcon.co.jp/en/eyecare/product/diag/oct/dri-_oct-1.html.
9. W. Drexler, U. Morgner, F. X. Kärtner, C. Pitris, S. A. Boppart, X. D. Li, E. P. Ippen, and J. G. Fujimoto, "In vivo ultrahigh-resolution optical coherence tomography," Optics Letters 24, 1221-1223 (1999).
10. L. Liu, J. A. Gardecki, S. K. Nadkarni, J. D. Toussaint, Y. Yagi, B. E. Bouma, and G. J. Tearney, "Imaging the subcellular structure of human coronary atherosclerosis using micro-optical coherence tomography," Nature Medicine 17, 1010-1014 (2011).
11. B. Povazay, K. Bizheva, A. Unterhuber, B. Hermann, H. Sattmann, A. F. Fercher, W. Drexler, A. Apolonski, W. J. Wadsworth, J. C. Knight, P. S. J. Russell, M. Vetterlein, and E. Scherzer, "Submicrometer axial resolution optical coherence tomography," Opt. Lett. 27, 1800-1802 (2002).
12. I. E. Commission, "IEC 60825-1 Edition 1.2 Safety of laser products," in *Equipment classification, requirements and user's guide*, (Geneva, Switzerland, 2001).
13. A. N. S. Institute, "American National Standard for Safe Use of Lasers," Z136.1 (2007).
14. J. M. Schmitt, "Optical coherence tomography (OCT): a review," Selected Topics in Quantum Electronics, IEEE Journal of 5, 1205-1215 (1999).
15. S. L. Marple Jr, "A tutorial overview of modern spectral estimation," in *Acoustics, Speech, and Signal Processing, 1989. ICASSP-89., 1989 International Conference on*, (IEEE, 1989), 2152-2157.
16. R. O. Schmidt, "Multiple emitter location and signal parameter estimation," Antennas and Propagation, IEEE Transactions on 34, 276-280 (1986).
17. J. Capon, "High-resolution frequency-wavenumber spectrum analysis," Proceedings of the IEEE 57, 1408-1418 (1969).
18. L. Jian and P. Stoica, "An adaptive filtering approach to spectral estimation and SAR imaging," Signal Processing, IEEE Transactions on 44, 1469-1484 (1996).
19. T. Yardibi, L. Jian, P. Stoica, X. Ming, and A. B. Baggeroer, "Source Localization and Sensing: A Nonparametric Iterative Adaptive Approach Based on Weighted Least Squares," Aerospace and Electronic Systems, IEEE Transactions on 46, 425-443 (2010).
20. Y. Takahashi, Y. Watanabe, and M. Sato, "Application of the maximum entropy method to spectral-domain optical coherence tomography for enhancing axial resolution," Appl. Opt. 46, 5228-5236 (2007).
21. A. Kartakoullis, E. Bousi, and C. Pitris, "Scatterer size-based analysis of optical coherence tomography images using spectral estimation techniques," Optics express 18, 9181-9191 (2010).
22. P. Stoica and R. L. Moses, *Introduction to Spectral Analysis* (Prentice Hall, 1997).
23. S. L. Marple, Jr., "A tutorial overview of modern spectral estimation," in *Acoustics, Speech, and Signal Processing, 1989. ICASSP-89., 1989 International Conference on*, 1989), 2152-2157 vol. 2154.
24. P. Stoica, E. G. Larsson, and J. Li, "Adaptive filter-bank approach to restoration and spectral analysis of gapped data," The Astronomical Journal 120, 2163 (2000).

The invention claimed is:

1. A method of obtaining an axial depth profile of a subject from an Optical Coherence Tomography (OCT) spectral image of the subject, the method comprising:
   a) obtaining a k-space interferogram of the OCT spectral image of the subject;
   b) uniformly reshaping the k-space interferogram to a quasi-stationary interferogram by extracting a source envelope;
   c) fitting a spectral estimation model to the quasi-stationary interferogram; and
   d) calculating the axial depth profile of the subject using the fitted spectral estimation model.

2. The method according to claim 1 wherein the spectral estimation model comprises a parametric model or a nonparametric model.

3. The method according to claim 1 wherein the step of uniformly reshaping the k-space interferogram comprises using a Hilbert transform to extract the envelope A as a function of k and sample depth, d; averaging A(k, d) across the dimension d to obtain the source envelope A(k); and dividing k-space interferogram signal by A(k) to obtain the quasi-stationary interferogram $S_{spre}(k)$.

4. The method according to claim 1 wherein the subject is a cellular structure.

* * * * *